United States Patent [19]
Holleron

[11] Patent Number: 5,163,915
[45] Date of Patent: Nov. 17, 1992

[54] SAFETY NEEDLE SET

[76] Inventor: Barry Holleron, 2523 Nacogdoches Rd., San Antonio, Tex. 78217

[21] Appl. No.: 817,537

[22] Filed: Jan. 7, 1992

[51] Int. Cl.$^5$ ............................................. A61M 5/32
[52] U.S. Cl. ..................................... 604/192; 604/263
[58] Field of Search ...................... 604/192, 263, 187; 206/365, 366

[56] References Cited

U.S. PATENT DOCUMENTS

| | | | |
|---|---|---|---|
| 4,623,336 | 11/1986 | Pedicano et al. | 604/192 |
| 4,781,697 | 11/1988 | Slaughter | 604/192 |
| 4,892,525 | 1/1990 | Hermann, Jr. et al. | 614/263 |
| 4,928,824 | 5/1990 | Barasch | 604/263 X |

*Primary Examiner*—John D. Yasko
*Attorney, Agent, or Firm*—Louis J. Bachand

[57] ABSTRACT

A safety needle set having a needle enclosing sheath with an enlarged portion to protect the user from injury.

10 Claims, 1 Drawing Sheet

SAFETY NEEDLE SET

TECHNICAL FIELD

This invention has to do with a safety needle set providing protection against inadvertent needle pricks and punctures such as may occur to medical personnel involved with the administration of medicaments, and more particularly with a safety needle set having a radially enlarged sheath portion and complementary cap around the needle-carrying hub so as to block pricks and punctures from happening upon careless misinsertion of the used needle into its enclosing sheath.

BACKGROUND

Medical professionals are repeatedly called upon to administer medications subcutaneously to patients. Typically, the medicament is administered by a needle which has been connected to the supply from a sterile containment arrangement comprising a sheath and a cap which holds the needle for connection and which is used to dispose of the used needle safely. Numerous medicaments are put up in small, premeasured quantities in disposable syringes. These syringes typically comprise a barrel containing the medicament, and a plunger movable through the barrel to dispense the medicament. A needle structure comprising a hub with a first needle to one side and a second needle to the other side is coupled to the syringe by breaking the syringe seal with the second needle. The first needle is used to deliver the medicament to the patient.

Needles typically are provided with a sleeve or sheath which encloses the needle to avoid contamination before use and to provide a means of disposal without leaving an exposed needle after use. It is with improvements in such needle containment devices that the present invention is concerned.

When withdrawing the needle from its sheath and when reinserting the needle into the sheath extreme care must be taken to avoid contact of the needle point with the hands and fingers. The usual mode of insertion, however, is to grip the needle or container attached to the needle with one hand and to hold the sheath with the other hand. In this manner the fingers on the sheath, typically thumb and forefinger, are in jeopardy of being stuck by the needle point if the needle insertion into the sheath is off target by even a very small distance.

In these times of highly infectious, even deadly diseases being rampant in care centers, and the great speed with which medical care is necessarily being given in overcrowded facilities, the need to protect the caregiver, and others in the facility is clear.

SUMMARY OF THE INVENTION

It is an object therefore to provide an improved protection system for medicament administration needles so as to block injury to the user, and possible infection, where the reinsertion of the needle is awry. It is another object to provide a modified form of needle cap and sheath containment having protection means integrated into the sheath construction so as to block inadvertent punctures of the operator's skin. It is a particular object to provide a novel form of needle sheath in which a portion of the sheath is radially enlarged to guard the operator's fingers from misdirected needle exposure. Yet another object is to provide a complementary cap for the enlarged sheath.

These and other objects of the invention to become apparent hereinafter are realized in a safety needle set for administration of medicament, the set comprising a hub having a hollow needle projecting axially therefrom; a needle-covering sheath having an annular portion securely engaged with the perimeter of the hub, an axially elongated portion extending from the hub-engaged portion and surrounding the projecting needle, and a radially enlarged portion extending outward of the hub-engaged portion opposite the axially elongated portion relative to the hub-engaged portion; and a cap adapted to close the radially enlarged portion against contamination of the hub and projecting needle, the hub and needle assembly being removable from the sheath and returnable thereto while holding the sheath between opposed fingers below the radially enlarged portion, the radially enlarged portion being of a size and material to resist advancement of the needle past the radially enlarged portion, whereby the radially enlarged portion blocks inadvertent sticking of fingers with the needle during movement of the needle relative to the sheath.

In this and like embodiments: the sheath and cap may each comprise rigid synthetic organic plastic; and, there is cooperating structure on the sheath radially enlarged portion and the cap for removably interfitting the sheath and cap in hub and needle contamination preventing relation.

In a preferred embodiment, the sheath radially enlarged portion is outwardly cupped for blocking lateral movement of the needle away from the hub beyond the radially enlarged portion, the sheath radially enlarged portion has an upstanding wall arranged to receive the needle and guide the needle to the hub, the sheath comprises rigid synthetic organic plastic, the cap comprises rigid synthetic organic plastic, the hub is metal such as aluminum or plastic, and there is cooperating structure on the cap and sheath for removably interfitting the cap and sheath radially enlarged portion at their opposed perimeters in hub and needle contamination preventing relation.

The invention further includes in combination: A safety needle set and a rigid plastic syringe having a barrel for containing medicament, a plunger and a needle mounting outlet arranged for coupling to a needle and delivery of medicament; the safety needle set comprising a hub having a first hollow needle projecting axially therefrom for delivery of medicament to a patient and a second hollow needle projecting oppositely from the first needle and adapted to pierce the syringe at the needle mounting outlet; a needle-covering sheath having an annular portion securely engaged with the perimeter of the hub, an axially elongated portion extending from the hub-engaged portion and surrounding the first projecting needle, and a radially enlarged portion extending outward of the hub-engaged portion; and a cap adapted to close s id radially enlarged portion against contamination of the hub and first and second needle, the hub and first needle being removable from the sheath and returnable thereto while holding the sheath between opposed fingers below the radially enlarged portion, the radially enlarged portion being of a size and material to resist advancement of the needle past the radially enlarged portion, whereby the radially enlarged portion blocks inadvertent sticking of fingers with the needle during movement of the needle relative to the sheath.

THE DRAWINGS

The invention will be further described in conjunction with the attached drawings in which.

DETAILED DESCRIPTION

Figure 1:
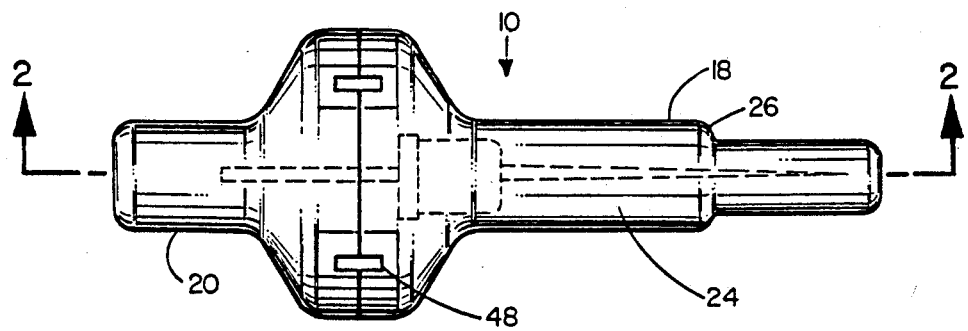
FIG. 1 is a side elevation of a safety needle set according to the invention.
Figure 2:
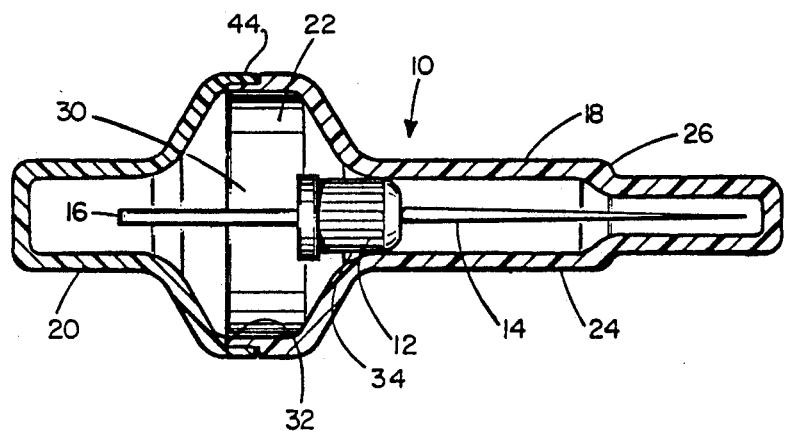
FIG. 2 is a vertical section thereof taken on line 2—2 in FIG. 1.
Figure 3:
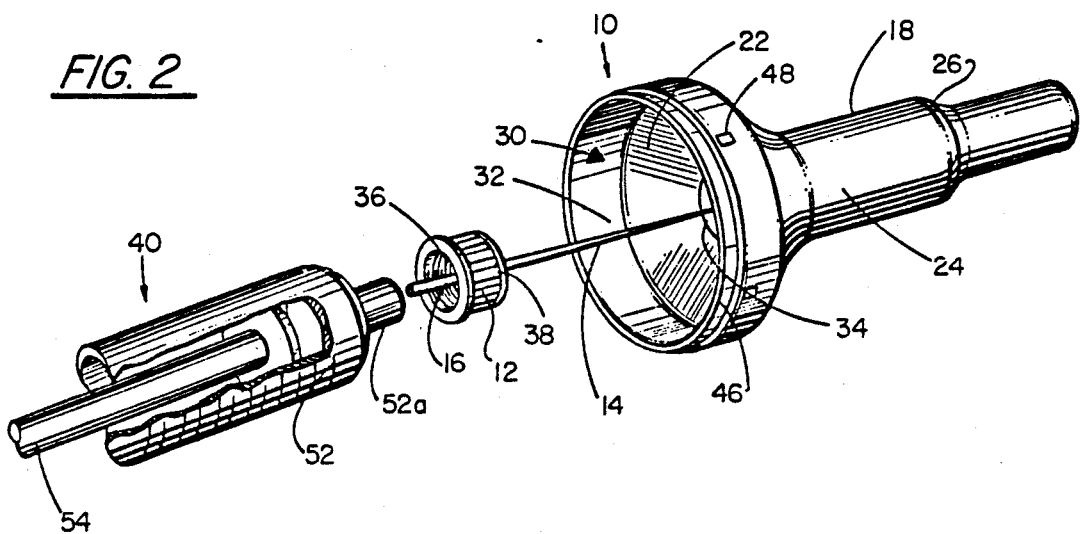
FIG. 3 is an exploded view of the safety needle set needle combined with a syringe for insertion in the sheath.

With reference to the drawings, In FIGS. 1 and 2 the invention safety needle set is shown at 10 to comprise a hub 12 having a hollow first needle 14 projecting therefrom for administration of medicament, a second needle 16 projecting therefrom oppositely from the first needle to pierce a medicament supply such as syringe 40 in FIG. 3, a sheath 18 covering the first projecting needle, and a cap 20 which in position closes the open end 22 of the sheath.

The sheath 18 is made of a suitable synthetic organic plastic such as styrene, vinyl, and olefinic polymers and copolymers, and may be translucent. The sheath 18 is suitably shaped to receive a needle 14 in guiding and enclosing relation. For this purpose the sheath 18 has an axially elongated portion 24 which is stepped at 26 to a small diameter as shown. Sheath 18 at its outer terminus forms mouth 34 sized to snugly fit around hub 12 sufficiently to resist inadvertent removal of the hub 12 and needle 14 assembly from the sheath 18. The sheath 18 axially elongated portion 24 opens outwardly at mouth 34 to sheath open end 22 formed by a radial enlargement of the sheath outward from the sheath axial portion 24. The resultant radially enlarged portion 30 is outwardly cup-shaped as shown, being surrounded by sidewall 32 which serve to deflect a needle 14 being inserted into the sheath 18 away from areas beyond the radially enlarged portion where hands and fingers may be found and to redirect the errant needle 14 into its proper place defined by the mouth 34 of the sheath axially elongated portion 24.

The hub 12 is formed of aluminum or plastic and internally threaded at 36 and knurled at exterior 38, see FIGS. 2 and 3. The hub 12 is threadable onto a syringe 40 (FIG. 3) with hub second needle 42 penetrating through the frangible wall (not shown) of the syringe for mounting the hub 12 and needle 14 assembly to the syringe as illustrative of various medicament supplies. The hub 12 is friction tightly fixed in the sheath 18 as best shown in FIG. 2.

The cap 20, suitably formed of a like plastic to the sheath 18 is oppositely cupped to the sheath open end 22 and provided with a knife edge 44 for interfitting securely with the edge 46 of the sheath, See FIG. 2. When first assembled the sheath 18 and cap 20 are tacked together by tabs 48 circumferentially arranged about the assembled cap and sheath to preserve sterility. See FIG. 1. To use the needle 14, the cap 20 and sheath 18 are separated by breaking the tabs 48 and pulling the cap and sheath apart.

In use, the hub 12 with needles 14 and 42 attached is removed from the sterile packaging provided by the cap 20 and sheath 18, the second needle 42 is punctured into the seal of a medicament container and the hub 12 is threaded onto the medicament supply container. The medicament is administered via the first needle 14. After administration of the medicament, the hub 12 with the medicament container still attached, and first needle 14 are safely disposed of by reinserting needle 14 into the sheath 18. The sheath enlarged portion 30 easily receives the needle blocking sticking of the fingers and hands of the operator by extending over the areas of the sheath 18 which are gripped by the fingers. Sheath sidewall 32 blocks undue lateral movement of the needle 14 as it is targeted toward the sheath axial elongated portion 24. As the needle 14 progresses along the sheath 18 the step 26 directs the needle into the smallest part of the sheath elongated portion, centering the needle. When fully inserted, the hub 12 is frictionally fitted in the sheath mouth 34, secure against inadvertent dislodgement.

With reference to FIG. 3, where a syringe 40 is shown arranged with the hub 12 and needles 14, 42, the syringe comprises a tubular barrel 52, suitably formed of a rigid synthetic organic plastic such as an ethylene or propylene polymer or copolymer, or a styrene or amide polymer which is resistant to medicaments to be applied therefrom and sufficiently stiff to permit injections to be made therewith. The barrel 52 terminates in an externally threaded barrel tip 52a. The syringe 40 further comprises a plunger 54 adapted to slide within the barrel 52 to deliver the medicament via second needle 42 through the hub 12 and into the internally hollow needle 14 for administration to a patient. After administration, the needle 14, 42 and hub 12 assembly is separated as already described, and disposed of safely through the provision of the sheath 18 enlarged portion.

The foregoing objects are thus achieved, including provision of an improved protection system for needles so as to block injury to the user, and possible infection, where the reinsertion of the needle is awry, provision of a modified form of syringe sheath having protection means integrated into the sheath construction so as to block inadvertent punctures of the operator's skin, and in particular provision of a novel form of needle sheath in which a radially enlarged portion of the sheath guards the operator's fingers from misdirected needle exposure.

I claim:

1. Safety needle set for administration of medicament, said set comprising a hub having a hollow needle projecting axially therefrom; a needle-covering sheath comprising a wall having an annular portion securely engaged with the perimeter of said hub, a wall continued extent forming an axially elongated portion integral with said hub-engaged portion and surrounding said projecting needle, and further wall continued extent forming a radially enlarged portion outward of and integral with said hub-engaged portion; a cap adapted to close said radially enlarged portion against contamination of said hub and projecting needle, said hub and needle being removable from said sheath and returnable thereto while holding said sheath between opposed fingers below said radially enlarged portion, said radially enlarged portion being of a size and material to resist advancement of said needle past said radially enlarged portion; and a plurality of circumferentially disposed tab means locking said sheath and cap together in the unused condition of said safety needle set, whereby said radially enlarged portion blocks inadvertent sticking of fingers with said needle during movement of said needle relative to said sheath.

2. Safety needle set according to claim 1, in which said sheath comprises rigid synthetic organic plastic.

3. Safety needle set according to claim 1, in which said cap comprises rigid synthetic organic plastic.

4. Safety needle set according to claim 1, including also cooperating structure on said sheath radially enlarged portion and said cap for removably interfitting said sheath and cap in hub and needle contamination preventing relation.

5. Safety needle set according to claim 1, in which said sheath radially enlarged integral portion is outwardly cupped for blocking lateral movement of said needle away from said hub beyond said radially enlarged portion.

6. Safety needle set according to claim 5, in which said sheath radially enlarged integral portion has an upstanding sidewall arranged to receive said needle and guide said needle to said hub.

7. Safety needle set according to claim 6, in which said sheath comprises rigid synthetic organic plastic.

8. Safety needle set according to claim 7, in which said cap comprises rigid synthetic organic plastic.

9. Safety needle set according to claim 8 including also cooperating structure on said cap and said sheath for removably interfitting said cap and said sheath radially enlarged portion in hub and needle contamination preventing relation said tab means being carried by said cap and tacked to said sheath.

10. In combination: A safety needle set and a rigid plastic syringe having a barrel for containing medicament, a plunger and a needle mounting outlet arranged for coupled to a needle and delivery of medicament; said safety needle set comprising a hub having a hollow needle projecting axially therefrom; a needle-covering sheath having an annular portion securely engaged with the perimeter of said hub, an axially elongated portion integral with and extending from said hub-engaged portion and surrounding said projecting needle, and a radially enlarged portion integral with and extending outward of said hub-engaged portion; and a cap adapted to close said radially enlarged portion against contamination of said hub and projecting needle, said hub and needle being removable from said sheath and returnable thereto while holding said sheath between opposed fingers below said radially enlarged portion, said radially enlarged portion being of a size and material to resist advancement of said needle past said radially enlarged portion; and a plurality of circumferentially disposed tab means locking said sheath and cap together in the unused condition of said safety needle set, whereby said radially enlarged portion blocks inadvertent sticking of fingers with said needle during movement of said needle relative to said sheath.

* * * * *